United States Patent [19]

Casey et al.

[11] 4,095,600

[45] Jun. 20, 1978

[54] NORMALLY-SOLID, BIOABSORBABLE, HYDROLYZABLE, POLYMERIC REACTION PRODUCT

[75] Inventors: Donald James Casey, Ridgefield; Martin Epstein, Norwalk, both of Conn.

[73] Assignee: American Cyanamid Company, Stamford, Conn.

[21] Appl. No.: 793,988

[22] Filed: May 5, 1977

Related U.S. Application Data

[62] Division of Ser. No. 691,749, Jun. 1, 1976, Pat. No. 4,048,256.

[51] Int. Cl.$^2$ .................... A61L 17/00; C08G 63/12; C08G 63/52
[52] U.S. Cl. .................... 128/335.5; 260/75 R; 260/75 UA; 260/78.3 R; 260/860; 424/78
[58] Field of Search ................ 260/860, 75 R, 75 UA, 260/78.3 R; 128/335.5; 424/78

[56] References Cited

U.S. PATENT DOCUMENTS

| | | | |
|---|---|---|---|
| 2,668,162 | 2/1954 | Lowe | 260/78.3 R |
| 2,676,945 | 4/1954 | Higgins | 260/78.3 R X |
| 3,297,033 | 1/1967 | Schmitt et al. | 128/335.5 |
| 3,468,853 | 9/1969 | Schmitt et al. | 260/78.3 R |
| 3,674,901 | 7/1972 | Shepherd et al. | 128/335.5 X |
| 3,867,190 | 2/1975 | Schmitt et al. | 128/335.5 X |
| 3,960,152 | 6/1976 | August et al. | 128/335.5 |

OTHER PUBLICATIONS

Korshak et al., in Academy of Sciences, USSR, Bulletin: Div. Chem. Sci. 1957, 889–893.

*Primary Examiner*—Thomas De Benedictis
*Attorney, Agent, or Firm*—James T. Dunn; Charles F. Costello, Jr.

[57] ABSTRACT

A normally-solid, bioabsorbable, hydrolyzable, polymeric reaction product of (A) a polyglycolic acid composition and (B) a polyester of diglycolic acid and an unhindered glycol and to the process of preparing the same and the use of said polymeric reaction product as a sterile surgical element and as a device for the controlled continuous administration of a predetermined dosage of a drug to a living animal.

2 Claims, No Drawings

NORMALLY-SOLID, BIOABSORBABLE, HYDROLYZABLE, POLYMERIC REACTION PRODUCT

This is a division of application Ser. No. 691,749, filed June 1, 1976, now U.S. Pat. No. 4,048,256.

CROSS-REFERENCE TO RELATED APPLICATION

This application is related to the U.S. application Ser. No. 418,138, filed Nov. 21, 1973, (Attorney's Docket 24,395) entitled HIGH MOLECULAR WEIGHT POLYESTER RESIN, THE METHOD OF MAKING THE SAME AND THE USE THEREOF in the names of Donald J. Casey and George C. Gleckler wherein the Donald J. Casey is the same Donald J. Casey who is a coinventor in the instant application. The aforementioned U.S. patent application (now abandoned) is incorporated herein by reference as is the streamlined continuation thereof Ser. No. 648,988, filed Jan. 14, 1976, (Attorney's Docket 26,122).

BACKGROUND OF THE INVENTION

Polyester resins have been prepared in the past by reacting such carboxylic acids as diglycolic acid with a dihydric alcohol such as a glycol but these polyester resins of the prior art were comparatively low molecular weight materials such as those having a molecular weight of about 3,000 to about 8,000 and many had an inherent viscosity of only about 0.25. These low molecular weight polyesters of diglycolic acid and glycols were not capable of forming self-supporting films and had been suggested for use as a propellant plasticizer, among other things. The Casey and Gleckler applications referred to hereinabove produce polyester resins from diglycolic acid and an unhindered glycol which have a molecular weight sufficiently high so as to provide a polymeric material possessing self-supporting, film-forming properties. Those polyester resins are normally solid, biodegradable, hydrolyzable polyester resins.

Polyglycolic acid is sometimes referred to as polyglycolide and sometimes referred to as polyhydroxy acetic ester. The polyglycolic acid has been a known material for a plurality of years and is known to be capable of forming self-supporting films and orientable fibers, which have found application as bioabsorbable surgical sutures. When any oriented monofilament is made from a polymeric material of sufficiently high molecular weight, of significant thickness, so as to provide the desired tensile strength, the monofilamentary material has a tendency to be stiffer than desired by some surgeons. It is known that stiffness in a filament varies as the 4th power of the diameter of the filament. However, when one combines chemically a high molecular weight polyglycolic acid composition with a polyester of diglycolic acid and an unhindered glycol, the resultant polymeric reaction product can be extruded into a monofilamentary material with significantly enhanced flexibility while still retaining its tensile strength.

FIELD OF THE INVENTION

The present invention is in the field of polymeric reaction products and, more particularly, a normally-solid, bioabsorbable, hydrolyzable, polymeric reaction product which can be prepared by heating a polyglycolic acid having a molecular weight of at least 30,000 at its melting point and adding to the molten polyglycolic acid selected amounts of a polyester of diglycolic acid and an unhindered glycol. The product thus produced can be converted into self-supporting films and fibrous materials which could find utility in the surgical field either as a sterile surgical element such as a suture or a ligature or as a device for the controlled continuous administration of a predetermined dosage of a drug to a living animal.

DESCRIPTION OF THE KNOWN PRIOR ART

The instant Applicants are aware of a publication entitled "Polyesters of Diglycolic Acid", Korshak et al., Academy of Sciences, USSR, Bulletin: Div. Chem. Sci. 1957, 889–93. Attention is also directed to the U.S. Pat. Nos. 2,668,162; 2,683,136; 2,676,945 and the U.S. Pat. No. 3,297,033, all of which patents are incorporated herein by reference as well as the literature reference by Korshak et al.

SUMMARY OF THE INVENTION

This invention relates to a normally-solid, bioabsorbable, hydrolyzable, polymeric reaction product of (A) a polyglycolic acid composition and (B) a polyester of diglycolic acid and an unhindered glycol wherein the amount of (B) used is between about 2% and 50%, by weight, based on the total weight of (A) and (B) and wherein (A), before reaction with (B), has a molecular weight of at least 30,000 and, preferably, between about 50,000 and 60,000 and (B), before reaction with (A), has a molecular weight sufficiently high so as to provide a polymeric material possessing self-supporting, film-forming properties. This invention also relates to a process for preparing said polymeric reaction product wherein the polyglycolic acid is heated at its melting point and there is added to the molten polyglycolic acid selected amounts of the polyester resin prepared from the diglycolic acid and the unhindered glycol and the heating of the blend is continued at or above the melting temperature of the resulting polymeric reaction product until the transesterification reaction is completed. This invention also relates to self-supporting films and filamentary materials produced from the transesterification product. This invention also relates to the use of such a transesterification product in the form of a device for the controlled continuous administration of a predetermined dosage of a drug to a living animal wherein the drug formulation is dispersed uniformly throughout said transesterification product.

The polymeric reaction products of the present invention can be prepared by reacting polyglycolic acid compositions with certain polyesters of diglycolic acid and unhindered glycol by use of a plurality of known chemical reactions. For instance, one can combine these two reaction entities by the use of certain linking compounds such as the diisocyanates or certain diacid dichlorides or certain diepoxide linking compounds. It is preferred, however, to make use of a transesterification reaction because this technique does not introduce any extraneous materials into the ultimate polymeric reaction product. One must avoid the use of any materials that may be toxic or those that may tend to impart significant diminished absorbability to the ultimate polymeric reaction product. Since it is known that aromatic compounds, when present in large amounts, will tend to diminish the bioabsorbable and hydrolyzable quality of products of this kind and, therefore, it is preferred to use aliphatic linking compounds although the aromatic linking compounds are used in such a small amount that the degree of diminished bioabsorbability is not objectionable.

POLYGLYCOLIC ACID

The polyglycolic acid is generally prepared from a substantially pure composition that consists essentially of α-glycolide and/or β-glycolide. The α-glycolide and its method of preparation are fully described in U.S. Pat. No. 3,457,280. The β-glycolide and its method of preparation are disclosed in the U.S. Pat. No. 3,435,008. The method for the purification of glycolide is disclosed in the U.S. Pat. No. 3,597,450. Each of these patents is incorporated herein by reference to avoid any unnecessary redundancy.

In making the polyglycolic acid composition to be used as one of the starting materials to produce the transesterification product of the present invention, one may make use of many of the polymerization catalysts that are known to be useful for the polymerization of glycolic acid or glycolide composition such as those disclosed in U.S. Pat. No. 2,676,945, namely, antimony trioxide and dibutyl tin dilaurate or the antimony trifluoride as disclosed in the U.S. Pat. No. 2,585,427. It is preferred to use the stannous chloride dihydrate which is disclosed in the U.S. Pat. Nos. 3,442,871 and 3,468,853. Each of these patents is incorporated herein by reference. Additionally, one can use stannous stearate, dibutyl tin dimethoxide, dibutyl tin diacetate, or dibutyl tin oxide and the like. The amount of the catalytic material used to polymerize the glycolic acid or the glycolide composition to the polyglycolic acid composition is generally varied between about 0.001 mol percent and 0.010 mol percent based on the total number of mols of purified glycolide composition used. It is preferred to use between about 0.001 mol percent and 0.005 mol percent of the catalyst based on the number of mols of purified glycolide composition used.

The polyglycolic acid composition may be a homopolymer or it may be a copolymer in which the glycolide is copolymerized with small quantities of the lactides. The U.S. Pat. No. 2,668,162 shows the polymerization of glycolide and indicates that one may advantageously prepare copolymers of glycolide with up to about 15 percent of other lactides such as D or L-lactide. This patent, too, is incorporated herein by reference.

In order to get even higher molecular weights than about 50,000–60,000, one can produce polyglycolic acid compositions that have chemical modification such as those shown in the U.S. Pat. No. 3,912,692 in which the modifier is inositol. The inherent viscosities of these modified polymers, when measured on a 0.5% solution of the polymer in hexafluoroacetone sesquihydrate at 30° C., may vary between about 0.8 and 1.6. This patent is also incorporated herein by reference.

One can also enhance the molecular weight of the polyglycolic acid and thereby produce an ultrahigh molecular weight material by subjecting the polyglycolic acid of conventional molecular weight to a prolonged heat treatment and vacuum. This is shown in the U.S. Pat. No. 3,890,283 issued in the names of the present co-Applicants. This patent is also incorporated herein by reference.

PREPARATION OF THE DIGLYCOLIC ACID POLYESTERS

The polyester resins used to produce the polymeric reaction products of the present invention are prepared by esterifying diglycolic acid and an unhindered glycol which polyesters are disclosed and claimed in the U.S. Patent Application Ser. No. 418,138, filed Nov. 21, 1973, which application is now abandoned but has been refiled as a streamlined continuation application having the Ser. No. 648,988, filed Jan. 14, 1976. Among the glycols which may be used to esterify the diglycolic acid to prepare the polyesters used in the present invention are ethylene glycol; diethylene glycol; 1,2-propylene glycol; 1,3-propylene glycol; 1,4-butylene glycol; dipropylene glycol; 1,5-pentanediol; 1,6-hexanediol; 1,7-heptanediol; 1,8-octanediol and the like. These and other glycols may be used individually or in combination with one another. These glycols when reacted with the diglycolic acid should be used in molar amounts substantially equivalent to the dicarboxylic acid although in order to achieve substantially full esterification, it is frequently desirable to use an excess of the glycol components in an amount of about 10 to 150 mole percent over and beyond the stoichiometrically calculated amount necessary to esterify all of the carboxyl groups of the diglycolic acid. As the molecular weight of the polyester increases during the esterification reaction, excess glycol is removed. When the esterification reaction is completed, the excess glycol, if any, can be removed.

In preparing the polyester resin used in preparing the transesterification product of the present invention, one can utilize as the catalytic material antimony trioxide in an amount varying between about 0.01% and 0.5%, by weight, based on the weight of the diglycolic acid. It is preferred to use between about 0.05% and 0.25%, by weight, of the antimony trioxide, based on the weight of diglycolic acid. The esterification reaction may be carried out at a temperature between about 125° C. and 250° C. and preferably between about 150° C. and 225° C. In order to achieve the desired high molecular weight polyester, the esterification reaction is carried out in three steps. The temperature ranges set forth hereinabove are applicable to all three steps. In the first step, the heating can be carried out over a period of about 1 to 5 hours at about 175° C. under an atmosphere of an inert gas such as nitrogen or carbon dioxide. In this first step, atmospheric pressure is generally used. In the second step, the pressure in the system is reduced to about 1.5 mm. of mercury and the heating is carried out for a period of from about 8 hours to about 24 hours. Ordinarily, the temperature would be about 175° C. In the third step, a higher vacuum (lower pressure) is applied in the order of magnitude of about 0.4 mm. of mercury and the period of time is generally between about 2 hours and 36 hours until a very viscous melt is produced. In the first step it is preferred to continue the heating for a period varying between about 2 hours and 3½ hours. In the second step it is preferred to use the heating time of between about 15 hours and 18 hours and in the third step it is preferred to use a heating time of between about 6 hours and 24 hours. The temperature selected will vary inversely with time, i.e., the higher the temperature, the shorter time interval and vice-versa.

In order to illustrate the process for the preparation of these polyester resins, the following examples are set forth in which all parts are parts by weight unless otherwise indicated. These examples are set forth primarily for purposes of illustration and any specific enumeration of detail contained therein should not be interpreted as a limitation on this application except as is indicated in the appended claims.

POLYESTER RESIN 1

Into a suitable polymerization reactor, fitted with a T-tube so that a capillary bubbler could be inserted through one port and the volatiles removed through the other port, there was introduced a blend of 26.8 parts of diglycolic acid (0.20 mol) (recrystallized from water using decolorizing charcoal) and 0.040 part of antimony trioxide. The blend of these two components was rinsed into the polymerization vessel with 24.8 parts of ethylene glycol (0.40 mol) that had been purified by treatment with sodium under nitrogen followed by distillation. A capillary bubbler was inserted into the polymerization reactor through a rubber seal so that the bottom of the bubbler was above the liquid in the reaction vessel. The system was purged with argon and then was immersed in a fluidized bed sand bath heated to 175° C. The vessel was adjusted until the sand was just above the level of the reactants, and then the capillary tube was pushed to the bottom of the liquid. The volatiles were distilled out of the reactor through the side port and collected in a trap. After 2¾ hours at 175° C., the pressure was gradually reduced so that after 45 minutes the pressure had reached 1.5 mm. of mercury. The reaction was continued for 16½ hours under these conditions. Thereupon the reaction vessel was immersed up to its neck, and the pressure was further reduced to about 0.4 mm. of mercury. After 8½ hours under these conditions, the reaction was discontinued. The product produced was a dark brown, clear, rubbery material having an inherent viscosity in hexafluoroacetone sesquihydrate of 0.78 (0.5% conc., 30° C.). The polymer was also soluble in chloroform. Analysis: Calculated for $C_6H_8O_5$:C,45.00; H,5.04; Found: C,44.61; H,5.04.

POLYESTER RESIN 2

Into a suitable polymerization vessel equipped as in Polyester Resin 1, there was introduced a mixture of 26.8 parts (0.20 mol) of diglycolic acid, 0.040 part of antimony trioxide and 30 parts of 1,3-propylene glycol (0.40 mol) which had been distilled under vacuum. The system was purged with argon and the mixture was heated for 2 hours at 175° C. whereupon the pressure was reduced over a 25 minute period to 1 mm. The reaction was continued for 15½ hours under these conditions. The tube was then inserted in the bath as far as possible and the pressure was further reduced to 0.4–0.5 mm. Heating was continued at about 175° C. under these reduced pressure conditions for an additional 24½ hours to produce a very viscous, amber product. After cooling the reaction mixture, 24.2 parts of a tough, flexible and opaque polymer was recovered. This material had an inherent viscosity of 0.85 in hexafluoroacetone sesquihydrate (0.5% conc., 30° C.). Analysis: Calculated for $C_7H_{10}O_5$:C,48.27; H,5.79; Found: C,48.18, 47.71; H,5.52,5.77.

POLYESTER RESIN 3

The procedure of Polyester Resin 1 was followed again but in this case 13.4 parts (0.10 mol) of diglycolic acid, 0.020 part of antimony trioxide and 16.7 parts of 1,2-propanediol (0.22 mol, treated with sodium under argon and distilled) were introduced into the polymerization reaction vessel. After 3 hours at 175° C. and atmospheric pressure under a blanket of argon gas, the pressure was gradually reduced and the reaction was continued for an additional 24 hours at 0.3 mm. of mercury with the argon slowly bubbled through the reaction mixture. The product was an amber, rubbery and transparent material with an inherent viscosity of 0.68 in hexafluoroacetone sesquihydrate (0.5% conc., 30° C.). Analysis: Calculated for $C_7H_{10}O_5$: C,48.27; H,5.79; Found: C,48.15; H,5.75. A solution of this polyester was prepared by dissolving 0.9 part of the polyester and 0.045 part of benzophenone in 3 volumes of hexafluoroacetone sesquihydrate. A film was cast from this solution, air-dried and then irradiated for 12 hours with a Hanovia 100 watt ultraviolet lamp at a distance of 3.25 inches. After irradiation, the tough, self-supporting film became highly swollen in hexafluoroacetone sesquihydrate but did not redissolve.

POLYESTER RESIN 4

The procedure of Polyester Resin 1 was followed in all essential details except that the side port was heated to facilitate the removal of the butanediol used in this example. Into the reaction vessel there was introduced 26.8 parts of diglycolic acid (0.20 mol), 0.040 part of antimony trioxide and 36.0 parts of 1,4-butanediol (0.40 mol, redistilled). The charge was heated under a nitrogen purge for 2 hours at 175° C. before the pressure was gradually reduced to 0.8 mm. of mercury. The reaction was permitted to continue at 175° C. and 0.5–0.8 mm. for 23½ hours. During the last 7½ hours, the polymerization vessel was immersed up to its neck in the 175° C. bath. At the end of the reaction the polymerization mixture was allowed to cool the room temperature under a nitrogen atmosphere. Further cooling in liquid nitrogen freed most of the polymer amounting to 36.5 parts (theoretically 37.6 parts) from the glass container; some additional polymer adhered strongly to the glass container and was not recovered. The polymer thus recovered was dissolved in chloroform and the solution was filtered. After the filtered solution was diluted seven-fold with acetone, the precipitated polymer was recovered by filtration, washed with acetone and dried to a constant weight at 40°–45° C. under reduced pressure. The polymer had an inherent viscosity of 0.65 (0.5% concentration in chloroform at 30° C.) and a melting point of 77° C. (differential thermal analysis). Analysis: Calculated for $C_8H_{12}O_5$:C, 51.06; H,6.43; Found: C,51.03; H,6.17

POLYESTER RESIN 5

In this example the reaction vessel used in Polyester Resin 1 was modified with a heated wide-bore side-arm tube so that the exit port would not become plugged with excess diol. There was introduced into this modified reaction vessel a mixture composed of 16.8 parts of diglycolic acid, (0.125 mol), 29.5 parts of hexamethylene glycol, (0.25 mol) and 0.025 part of antimony trioxide. After the reaction mixture had been heated for 2 hours at 175° C. the pressure was gradually reduced to 0.8 mm. of mercury and the polymerization vessel was slowly lowered into the sand bath so as to maintain a steady evolution of excess diol. After the bulk of the excess diol had been removed, the pressure was reduced further to 0.2–0.3 mm. and the reaction was continued until a very viscous melt was achieved. The resulting cloudy, tough, amber polymer had an inherent viscosity of 0.70 in chloroform (0.5% conc., 30° C.). Reprecipitation of this material was effected by cooling an acetone solution of the polymer to −78° C. and then removing the acetone under reduced pressure at −50° − −60° C. The caked residue was further dried under reduced pressure at room temperature. Analysis: Calculated for $C_{10}H_{16}O_5$:C,55.54; H,7.46; Found: C,54.97; H,7.43.

In order that the concept of the present invention may be more fully understood, the following examples are set forth in which all parts are parts by weight unless otherwise indicated. These examples are set forth primarily for the purposes of illustration and any specific enumeration of detail contained therein should not be interpreted as a limitation of the case except as is indicated in the appended claims.

EXAMPLE 1, (PART 1).

Into a suitable reaction vessel preheated to 140° C., that has been purged with nitrogen gas, there is charged a mixture consisting of 160 parts of molten glycolide into which was placed 0.0032 part (0.002%) of stannous chloride dihydrate and 0.128 part (0.08%) of lauryl alcohol. The reaction vessel is heated to 218° C. with constant stirring for 60 minutes after charging the molten glycolide to the reactor. The system is then placed under a 40 mm. vacuum for about 30 minutes. The polyglycolic acid at this point has an inherent viscosity in hexafluoroacetone sesquihydrate of 0.94 when measured on a 0.5% solids solution at 30° C.

EXAMPLE 1, (PART 2)

While maintaining the polyglycolic acid at about 218° C. under a blanket of nitrogen, 40 parts of poly(1,4-butylene diglycolate), having an inherent viscosity in chloroform of 0.43 when measured on a 0.5% solids solution at 30° C., is added to the molten polyglycolic acid with constant stirring. Samples of the transesterified copolymer were removed from the reaction vessel at intervals of 40 minutes, 80 minutes and 120 minutes after the addition of the poly(butylene diglycolate). The samples all had inherent viscosities of about 0.68-0.69 when measured on a 0.5% solids solution in hexafluoroacetone sesquihydrate at 30° C. and the samples when analyzed by nuclear magnetic resonance showed a content of 20.5 weight percent of the poly(1,4-butylene diglycolate) and 79.5% weight percent of the polyglycolic acid. The samples of the transesterified product were ground to a ten mesh size in a Wiley mill and dried in a vacuum oven at less than 1 mm. of mercury and at 135° C. for about 24 hours before being fabricated into a film and also into a fiber.

EXAMPLES 2-13 INCLUSIVE

The basic procedure of Example 1 (part 2) was followed with the exceptions noted hereinbelow. In the Examples 2, 3 and 4 a polyglycolic acid material was used having an inherent viscosity of 1.12 when measured on a 0.5% solids solution in hexafluoroacetone sesquihydrate at 30° C. The amount of the poly(1,4-butylene diglycolate) was 5%. In Examples 5, 6 and 7 the polyglycolic acid had an inherent viscosity of 0.91, same basis of measurement, and the amount of the poly(1,4-butylene diglycolate) was 10%. In Examples 8, 9 and 10 the inherent viscosity of the polyglycolic acid was 1.03, same basis of measurement, and the amount of the poly(1,4-butylene diglycolate) was 15%. In Examples 11, 12 and 13 the polyglycolic acid used had an inherent viscosity of 0.94, same basis of measurement, and the amount of the poly(1,4-butylene diglycolate) was 20%. These percentages are by weight based on the total weight of (A) and (B), namely, the polyglycolic acid and the polyester. The transesterification time for the Examples 2, 5, 8 and 11 was 40 minutes. The transesterification time for the Examples 3, 6, 9 and 12 was 80 minutes. The transesterification time for the Examples 4, 7, 10 and 13 was 120 minutes. Further details of these Examples are set forth in Table I hereinbelow. These examples were carried out in a cone-vertical mixer manufactured by Atlantic Research. The inherent viscosity of the poly(1,4-butylene diglycolate) in all of these examples was 0.43 when measured on a 0.5% solids solution in chloroform at 30° C. The polyglycolic acid homopolymer when subjected to the same heating conditions for varying periods of time in the absence of any poly(alkylene diglycolate) would undergo a diminution of the inherent viscosity. For instance, a PGA having a starting inherent viscosity of 1.01 would show a decrease in inherent viscosity to 0.99 in 30 minutes; to 0.98 in 60 minutes; to 0.98 in 90 minutes and to 0.94 in 120 minutes if held under a blanket of nitrogen at 222° C. for these periods of time.

TABLE I

TRANSESTERIFICATION COPOLYMER

| Examples | NMR $\eta$inch | Wt % 1,4-BDG | $t_g$ ° C. | DSC Endotherm, ° C. Start | Peak | End. |
|---|---|---|---|---|---|---|
| 2 | 0.94 | 4.8 | 37° | 196 | 223 | 228 |
| 3 | 0.88 | 5.0 | 37° | 194 | 221 | 228 |
| 4 | 0.87 | 4.8 | — | 196 | 221 | 229 |
| 5 | 0.81 | 9.3 | — | 189 | 220 | 226 |
| 6 | 0.78 | 9.0 | 34 | 181 | 217 | 225 |
| 7 | 0.77 | 9.3 | 34 | 181 | 215 | 221 |
| 8 | 0.76 | 15.2 | 29 | 185 | 215 | 222 |
| 9 | 0.73 | 15.0 | 29 | 172 | 204 | 210 |
| 10 | 0.72 | 14.4 | — | 162 | 199 | 204 |
| 11 | 0.69 | 20.3 | 25 | 170 | 208 | 213 |
| 12 | 0.68 | 20.8 | 25 | 152 | 196 | 203 |
| 13 | 0.68 | 20.5 | 25 | 130 | 185 | 196 |

EXAMPLE 14

Example 1 (part 2) is repeated in all essential details except that there is used a polyglycolic acid having an inherent viscosity of 0.85, measured as before, and the modifier was 10% by weight of poly(1,4-butylene diglycolate) having an inherent viscosity of 0.43 when measured on a 0.5% solids solution in chloroform. The transesterification was carried out in a cone-vertical mixer and the transesterification time was 25 minutes at about 222° C. The resulting transesterification product had an inherent viscosity of 0.75 when measured on a 0.5% solids solution of the copolymer in hexafluoroacetone sesquihydrate. The resulting copolymer had a melting point range of from 194° C. to 229° C. when measured on a differential scanning calorimeter.

EXAMPLE 15

Example 14 is repeated in all essential details except that the transesterification time was 240 minutes and the inherent viscosity of the resulting copolymer was 0.66 as measured on the same solids solution in hexafluoroacetone sesquihydrate. The melting point range as measured on a differential scanning calorimeter was 173°-213° C.

EXAMPLES 16, 17, AND 18

Example 14 is repeated in all essential details except that there was used a polyglycolic acid having an inherent viscosity of 1.12 and 10% of poly(1,3-propylene diglycolate) having an inherent viscosity of 0.65 when measured on a 0.5 % solids solution in chloroform at 30° C. The results of these examples are set forth hereinbelow in Table II.

TABLE II

| Examples | Time | η inh[1] | $t_g$ | DSC-Endotherm, °C.[2] | | | NMR[3] Wt% 1,3-PDG |
|---|---|---|---|---|---|---|---|
| | | | | Start | Peak | End | |
| 16 | 40 min. | 0.75 | 34 | 195 | 224 | 233 | 9.8 |
| 17 | 120 min. | 0.69 | 36 | 189 | 218 | 225 | 9.9 |
| 18 | 240 min. | 0.63 | 34 | 179 | 211 | 216 | 10.5 |

[1]Inherent viscosity of the transesterified copolymer in hexafluoroacetone sesquihydrate.
[2]Differential scanning calorimeter.
[3]NMR = Nuclear Magnetic Resonance.

EXAMPLE 19

Into a suitable reaction vessel equipped with a stirrer there was introduced simultaneously 70 parts of a polyglycolic acid, having an inherent viscosity of 1.05 when measured on a 0.5% solids solution in hexafluoroacetone sesquihydrate at 30° C., and 30 parts of a poly(1,4-butylene diglycolate) having an inherent viscosity of 0.81 when measured on a 0.5% solids solution in hexafluoroacetone sesquihydrate at 30° C. The two materials are melted together for 30 minutes and the heating was continued at about 235°0 C. under a blanket of nitrogen gas for an additional 50 minutes. The resultant copolymer had an inherent viscosity of 0.73 when measured as before, a weight % content of 29.3% of poly(1,4-butylene diglycolate), when measured by nuclear magnetic resonance; a glass transition temperature of 18° C. and a melting point of 183° C. when measured by differential scanning calorimetry and 180°–190° by hot stage microscopy. When the transesterified copolymer was reprecipitated from hexafluoroacetone sesquihydrate into dioxane, the inherent viscosity was 0.74 and the weight % of the poly(1,4-butylene diglycolate) was 27.7% when measured by nuclear magnetic resonance.

EXAMPLES 20–29 INCLUSIVE

Varying amounts of polyglycolic acid were transesterified at 235° C. under a blanket of nitrogen with poly(1,3-propylene diglycolate). The polyglycolic acid, in each instance, had an inherent viscosity of 1.05 as measured before. The poly(1,3-propylene diglycolate) used in Examples 20, 24 and 25 had an inherent viscosity of 0.58 when measured on a 0.5% solids solution in chloroform at 30° C. The remaining examples, namely, Examples 21, 22, 23, 26, 27, 28 and 29 contained a poly(1,3-propylene diglycolate) having an inherent viscosity of 0.65 when measured on a 0.5% solids solution in chloroform at 30° C. The resultant transesterified copolymer was dissolved in hexafluoroacetone sesquihydrate and cast films were prepared therefrom by depositing the solution on a substrate and evaporating the solvent. Tensile properties of the cast films were determined and the results are set forth in Table III hereinbelow.

TABLE III

PGA/Poly(1,3-Propylene diglycolate) Copolymers

| Examples | 1,3-PDG Charged, % | Reaction Time, min. | Copolymer ηinh | ¹H-NMR Wt% 1,3-PDG[1] | Tensile Properties of Cast Films | | |
|---|---|---|---|---|---|---|---|
| | | | | | Tens. Str., psi | Elong. % | Sec. Mod. at 10%, psi |
| 20 | 40 | 25 | 0.69 | 42.6 | 2300 | 102 | 20,600 |
| 21 | 30 | 25 | 0.64 | 30.0 | 1580 | 8 | — |
| 22 | 40 | 25 | 0.58 | 44.1 | 1400 | 27 | 12,600 |
| 23 | 50 | 25 | 0.44 | 52.8 | 1750 | 27 | 14,000 |
| 24 | 30 | 50 | 0.53 | 31.5 | 903 | 3 | — |
| 25 | 50 | 50 | 0.49 | 60.0 | 564 | 18 | 4,800 |
| 26 | 30 | 50 | 0.65 | 27.3 | — | — | — |
| 27 | 40 | 50 | 0.62 | 41.8 | 2800 | 91 | 24,700 |
| 28 | 50 | 50 | 0.46 | 56.4 | 1650 | 50 | 12,200 |
| 29 | 40 | 120 | 0.52 | 36.8 | — | — | — |

[1]Copolymers prepared with 30% and 40% of the modifier were purified by dissolving the "as-made" compositions in hexafluoroacetone sesquihydrate and reprecipitating the copolymers into dioxane. The purified samples were used for η inh, NMR, and tensile masurements. Copolymers containing 50% of the 1,3-PDG were not reprecipitated.

EXAMPLE 30

Into a suitable reaction vessel there was introduced 90.9 parts of a dried polyglycolic acid material having an inherent viscosity of 1.05 and 9.1 parts of poly(1,2-propylene diglycolate) having an inherent viscosity of 0.40 as measured previously on a chloroform solution. The two component mix is melted at 235° C. using a continuous nitrogen blanket purge. After the melt has been completed, the mixture is stirred for a reaction time of about 25 minutes. The mass is then cooled under nitrogen and the solid is ground in a Wiley mill. An inherent viscosity of 0.92 is measured on the copolymer.

EXAMPLE 31

Example 30 is repeated in all essential details except that the amount of the polyglycolic acid used was about 83.3 parts and the poly(1,2-propylene diglycolate) was about 16.7 parts. An inherent viscosity of 0.81 was measured for this copolymer.

EXAMPLE 32

Example 1 (part 1) is repeated in all essential details except that there is used 144 parts of the glycolide and 16 parts of lactide to produce a copolymer of glycolide and lactide in a 90/10 weight ratio. Example 1 (part 2) was then repeated in all essential details using 160 parts of the copolymer and 40 parts of poly(1,4-butylene diglycolate). A transesterification copolymer was produced having properties similar to those produced in Example 1.

EXAMPLE 33

Example 32 was repeated in all essential details except that there was used, to produce the copolymer of the glycolide and the lactide, 136 parts of the glycolide and 24 parts of the lactide to provide an 85/15 weight ratio. The ultimate transesterification copolymer with the poly(1,4-butylene diglycolate) was lower melting than the copolymer produced according to Example 32.

EXAMPLE 34

Example 32 is repeated in all essential details except that the copolymer was composed of about 152 parts of the glycolide and 8 parts of the lactide to provide a 95/5 weight ratio. The ultimate transesterification copolymer had properties similar to those produced in Examples 32.

The transesterification reactions set forth in the examples hereinabove have been carried out for varying periods of time. Longer reaction times result in increased transesterification as indicated by the steadily decreasing melting points for copolymers of identical composition. Similarly, as the degree of transesterification is increased, a greater number of carbonyl carbon signals are detected in $^{13}$C-NMR spectra of the copolymers. Depending on the polymer properties desired, the transesterification reaction can be carried out for a period of time varying between about 25 minutes and 240 minutes.

The expression "a polyglycolic acid material or composition", as used herein, encompasses homopolymers of glycolic acid or glycolide as well as copolymers of lactides such as lactide per se and disalicylide with glycolic acid or glycolide as is shown in the U.S. Pat. No. 2,668,162.

The polyglycolic acid composition, if it contains small amounts of a lactic acid such as up to about 15% by weight and correspondingly at least 85% by weight of the glycolic acid or glycolide, may be a block copolymer or a random copolymer. If it is a block copolymer, the units from the glycolic acid or glycolide will be linked to one another and the units from the lactic acid or lactide material will also be linked to one another and the two separate types of blocks will be linked together one or more times in the total polymeric structure. This can be accomplished by utilizing the monomeric materials and polymerizing them in keeping with the teaching of the prior art. An alternative approach would be to prepare the homopolymers of glycolic acid and the homopolymers of lactic acid separately and to introduce the selected amounts of these separate homopolymers into a suitable reaction vessel and cause them to interreact, thereby producing a copolymeric material containing blocks of the two separate homopolymers joined together in the copolymer. The block copolymeric materials have, in many respects, advantages over the random copolymers in which the units of the respective moieties are distributed throughout the polymer chain in a random fashion. The language, the polyglycolic acid composition, is intended to encompass both the block copolymers or the random copolymers and mixtures thereof. When the polyglycolic acid composition is co-reacted with the diglycolic acid polyester, again random copolymers may be formed but it is more likely that the block copolymers will be formed. The ultimate reacted polymeric material from these two principal components may be entirely block copolymers or mixtures of block copolymers and random copolymers or exclusively random copolymers.

The transesterification reaction products of the present invention can be used to manufacture a device for the controlled continuous administration of the predetermined dosage of a drug to a living animal. The normally-solid, biodegradable, bioabsorbable, hydrolyzable transesterification products of the present invention are particularly useful in formulating pharmaceutical compositions. Illustrative of such pharmacologically active compounds which can be employed include the following: nitroglycerine, anti-viral agents, triamicinolone acetonide, enzymes, i.e., streptokinase, papain, aspariginase, etc., nitroimidazole, nitrofurdentoin, 17α-ethynyl-17β-hydroxy-5(10)estren-3-one, α-cyclohexyl-α-phenyl-1-pipiridine-propanol hydrochloride, pilocarpine, acetazolamide, prostaglandins, diethylcarbamazine.

For a specific example, dosage rates for the biologically active compounds recited herein are not given. However, such materials are well known and dosage rates are established for them in different applications. By application of this knowledge, those skilled in the art can formulate controlled release biologically or otherwise active composition in accordance with this invention.

Medicine, medication or other biologically active compositions including drugs, may be incorporated into a device comprising the polymeric reaction products of the present invention by various techniques such as by solution methods, suspension methods or melt pressing.

For instance, 52 mg. of pilocarpine hydrochloride was dissolved in 95% ethyl alcohol (0.5 ml.) and 0.5 ml. of said solution was added to a solution of the transesterification reaction product of Example 23(52.8% poly(1,3-propylene diglycolate) by NMR) (0.95 g. polymer dissolved in 3 ml. of dioxane). The resulting solution was cast into a film and after drying in air and then under vacuum, the film was slightly hazy, strong and cold drawable.

As an alternative approach, finely ground pilocarpine hydrochloride (50 mg.) was added to a solution of the transesterification reaction product, as in the preceding method, except that the hydrochloride was in suspension. The mixture was agitated until a good dispersion was obtained and the dispersion was then cast into a film and dried as before.

The film from the solution method set forth hereinabove was cut into large pieces and put between aluminum foils separated by 6 mil shims. The "sandwich" was pressed between chrome plated steel plates at a platen temperature of about 100° C. for 30 seconds after preheating for 3 minutes. The sandwich was allowed to stand overnight in a desiccator to give the polyester transesterification reaction product time to crystallize.

Various other delivery devices may be manufactured from these transesterification compositions to administer drugs via a number of routes. For example, an intrauterine device for releasing an anti-fertility agent at a controlled rate for a prolonged period of time; a medical bandage for use in the continuous administration of controlled quantities of systemically active drugs over a prolonged period of time by absorption through the external body skin or mucosa; a strip which could be inserted between the gum and the cheek so that absorption of the medicament at a predetermined interval through the buccal mucosa into the bloodstream may take effect. Drugs could also be incorporated into fine particles of these polyester resin transesterification reaction products and subsequently a dispersion of these particles could be injected parenterally, subcutaneously, intramuscularly, etc., at which site the polymeric material would slowly biodegrade and release the drug over a prolonged period of time. Other methods of drug administration can be envisaged and those skilled in the art can manufacture controlled release devices from these compositions in accordance with the present invention.

Certain of the polyester resin transesterification reaction products of the present invention have elastomeric characteristics whereas other transesterification products of the present invention, with higher melting points and some measure of crystallinity, may be formed into filaments which display excellent tensile strength and thereby are usable individually or collectively, such as in braided form, as a sterile suture or ligature.

Several of these transesterification materials of the present invention may be used as a coating material on sutures and ligatures whether as individual fibers or braided structures. For instance, the polyester transesterification products of Examples 23, 25, or 28 would be suitable for use as suture braid coatings because these polymeric materials are amorphous and elastomeric. When the polyester transesterification products of the present invention are to be used as a braid coating to improve the knot run-down characteristics of a suture or ligature, the transesterification product is dissolved in a suitable solvent such as dioxane and the filament and braided structure is coated with the solution of the transesterification product by dipping, brushing, spraying and the like and the solvent is then evaporated, thereby depositing a film of the transesterification product on the filaments or the braid. The lower melting transesterification products of the present invention are particularly good for coating the ligatures and sutures in order to impart the desired degree of slipperiness thereto. These coatings can be applied to the polyglycolic acid sutures and ligatures as disclosed in the U.S. Pat. No. 3,297,033 which patent is incorporated herein by reference. Other suture materials such as those made from polyethyleneterephthalate may also be coated with films of the transesterification products of the present invention.

The following example shows a method for coating braided polyglycolic acid filaments with the transesterification reaction products of the present invention.

EXAMPLE 35

Polyglycolic acid filamentary braid was dip coated with the transesterification reaction product consisting of 50% PGA and 50% poly(1,3-propylene diglycolide) [EX. 28] by passing the braid through either a 1%, 2% or 4% (wt./vol.) solution of the transesterification product in dioxane. The wet braid was dried at room temperature to volatilize the solvent and leave a 0.93% to 4.6%, by weight, coating (based on the weight of the braid) of the transesterification reaction product deposited on the braid surface.

Comparative knot run-down tests were made with the thus coated braid, and an uncoated polyglycolic acid control. These evaluations were carried out by looping the braid around a rigid rod, casting a knot in the upper part of the braid and subjectively estimating the relative ease with which the knot could be slipped down the length of the braid and tightened around the rod. In these tests, an improvement in slip was noted for the coated braid.

In addition to using the transesterification products of the present invention as devices for the controlled continuous administration of a predetermined dosage of a drug and the use in making filaments for sutures and ligatures in a sterile state, and the use of the transesterification reaction products as a coating for braided sutures and ligatures, one could use these transesterification products to make solid products by molding or machining so as to produce orthopedic pins, clamps and the like, or fibrillar products made from filaments of these transesterification products which can be knitted or woven for use as burn dressings, gauze bandages and the like. A process for packaging sterile surgical elements such as sutures, ligatures, burn dressings, gauze bandages and the like as well as the packages themselves are shown in the U.S. Pat. No. 3,728,839 which patent is incorporated herein by reference.

We claim:

1. A sterile surgical element produced from the polymeric reaction product of (A) a polyglycolic acid composition and (B) a polyester of diglycolic acid and an unhindered glycol; wherein the amount of (B) used is between about 2% and 50%, by weight, based on the total weight of (A) and (B); wherein (A), before reaction with (B), has a molecular weight of at least 30,000 and (B), before reaction with (A), has a molecular weight sufficiently high so as to provide a polymeric material possessing self-supporting film-forming properties.

2. A sterile surgical element according to claim 1 in the form of a suture or ligature.

* * * * *